(12) United States Patent
Prystowsky et al.

(10) Patent No.: US 10,278,607 B2
(45) Date of Patent: *May 7, 2019

(54) SYSTEM AND METHOD FOR PROCESSING AND PRESENTING ARRHYTHMIA INFORMATION TO FACILITATE HEART ARRHYTHMIA IDENTIFICATION AND TREATMENT

(71) Applicant: Braemar Manufacturing, LLC, Eagan, MN (US)

(72) Inventors: Eric N. Prystowsky, Carmel, IN (US); Lev Korzinov, San Diego, CA (US); Eric Baumann, San Diego, CA (US); Scott Denis, Murrieta, CA (US); Manuel E. Jaime, Solana Beach, CA (US); Justin James, Dan Diego, CA (US)

(73) Assignee: BRAEMAR MANUFACTURING, LLC, Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/593,237

(22) Filed: Jan. 9, 2015

(65) Prior Publication Data

US 2015/0190067 A1 Jul. 9, 2015

Related U.S. Application Data

(63) Continuation of application No. 13/046,673, filed on Mar. 11, 2011, now Pat. No. 8,945,019, which is a
(Continued)

(51) Int. Cl.
*A61B 5/00* (2006.01)
*A61B 5/046* (2006.01)
(Continued)

(52) U.S. Cl.
CPC ............ *A61B 5/046* (2013.01); *A61B 5/0006* (2013.01); *A61B 5/0245* (2013.01);
(Continued)

(58) Field of Classification Search
CPC ..... A61B 5/046; A61B 5/0006; A61B 5/0245; A61B 5/7246; A61B 5/7282; A61B 5/742
See application file for complete search history.

(56) References Cited

U.S. PATENT DOCUMENTS

| 3,832,994 A | 9/1974 | Bicher et al. |
| 3,921,624 A | 11/1975 | Vogelman |

(Continued)

FOREIGN PATENT DOCUMENTS

| EP | 360412 A1 | 3/1990 |
| EP | 0505627 A2 | 9/1992 |

(Continued)

OTHER PUBLICATIONS

Japanese Patent Application No. 2006-541106, Dispatch date May 18, 2010, Decision of Refusal, 9 pages, including translation.
(Continued)

*Primary Examiner* — Scott Getzow
(74) *Attorney, Agent, or Firm* — Ropes & Gray, LLP

(57) ABSTRACT

A system and method for presenting information relating to heart data can involve operations including identifying arrhythmia events in physiological data obtained for a living being, receiving human assessments of at least a portion of the arrhythmia events, determining a measure of correlation between the human assessments and the identified events, and selectively presenting information regarding the identified events based on the measure of correlation. The operations can also include identifying atrial fibrillation events in physiological data obtained for a living being, obtaining heart rate data for the living being, and presenting informa-
(Continued)

tion regarding the heart rate data and duration of the atrial fibrillation events together with a common time scale to pictographically represent heart rate trend with atrial fibrillation burden during a defined time period.

7 Claims, 6 Drawing Sheets

Related U.S. Application Data continuation of application No. 11/739,037, filed on Apr. 23, 2007, now Pat. No. 7,907,996, which is a continuation of application No. 10/760,122, filed on Jan. 16, 2004, now Pat. No. 7,212,850.

(60) Provisional application No. 60/525,386, filed on Nov. 26, 2003.

(51) Int. Cl.
*A61B 5/0245* (2006.01)
*A61B 5/044* (2006.01)

(52) U.S. Cl.
CPC .......... *A61B 5/7246* (2013.01); *A61B 5/7282* (2013.01); *A61B 5/742* (2013.01); *A61B 5/044* (2013.01)

(56) References Cited

U.S. PATENT DOCUMENTS

| | | | |
|---|---|---|---|
| 4,173,971 | A | 11/1979 | Karz |
| 4,339,800 | A | 7/1982 | Woods |
| 4,364,397 | A | 12/1982 | Citron et al. |
| 4,531,527 | A | 7/1985 | Reinhold, Jr. et al. |
| 4,622,979 | A | 11/1986 | Katchis et al. |
| 4,625,278 | A | 11/1986 | Wong |
| 4,630,204 | A | 12/1986 | Mortara |
| 4,635,646 | A | 1/1987 | Gilles et al. |
| 4,756,706 | A | 7/1988 | Kerns et al. |
| 4,791,933 | A | 12/1988 | Asai et al. |
| 4,794,532 | A | 12/1988 | Leckband et al. |
| 4,827,943 | A | 5/1989 | Bornn et al. |
| 4,883,064 | A | 11/1989 | Olson et al. |
| 4,920,489 | A | 4/1990 | Hubelbank et al. |
| 4,938,228 | A | 7/1990 | Righter et al. |
| 4,951,681 | A | 8/1990 | Mortara |
| 4,952,928 | A | 8/1990 | Carroll et al. |
| 4,958,641 | A | 9/1990 | Digby et al. |
| 4,977,899 | A | 12/1990 | Digby et al. |
| 4,989,610 | A | 2/1991 | Patton et al. |
| 5,025,795 | A | 6/1991 | Kunig |
| 5,058,597 | A | 10/1991 | Onoda et al. |
| 5,080,105 | A | 1/1992 | Thornton |
| 5,090,418 | A | 2/1992 | Squires et al. |
| 5,113,869 | A | 5/1992 | Nappholz et al. |
| 5,181,519 | A | 1/1993 | Bible |
| 5,191,891 | A | 3/1993 | Righter |
| 5,197,479 | A | 3/1993 | Hubelbank et al. |
| 5,206,807 | A * | 4/1993 | Hatke ............... A61B 5/0205 600/484 |
| 5,216,425 | A | 6/1993 | Erhage |
| 5,217,021 | A | 6/1993 | Steinhaus et al. |
| 5,223,844 | A | 6/1993 | Mansell et al. |
| 5,226,431 | A | 7/1993 | Bible et al. |
| 5,228,450 | A | 7/1993 | Sellers |
| 5,238,001 | A | 8/1993 | Gallant et al. |
| 5,305,202 | A | 4/1994 | Gallant et al. |
| 5,309,920 | A | 5/1994 | Gallant et al. |
| 5,350,404 | A | 9/1994 | Adams |
| 5,365,935 | A | 11/1994 | Righter et al. |
| 5,398,183 | A | 3/1995 | Elliott |
| 5,416,695 | A | 5/1995 | Stutman et al. |
| 5,417,222 | A | 5/1995 | Dempsey et al. |
| 5,421,342 | A | 6/1995 | Mortara |
| 5,452,339 | A | 9/1995 | Siu et al. |
| 5,490,515 | A | 2/1996 | Mortara |
| 5,501,229 | A | 3/1996 | Selker et al. |
| 5,513,645 | A | 5/1996 | Jacobson et al. |
| 5,522,396 | A | 6/1996 | Langer et al. |
| 5,544,661 | A | 8/1996 | Davis et al. |
| 5,546,950 | A | 8/1996 | Schoeckert et al. |
| 5,549,113 | A | 8/1996 | Halleck et al. |
| 5,568,121 | A | 10/1996 | Lamensdorf |
| 5,568,126 | A | 10/1996 | Andersen et al. |
| 5,576,689 | A | 11/1996 | Queen |
| 5,581,369 | A | 12/1996 | Righter et al. |
| 5,634,468 | A | 6/1997 | Platt et al. |
| 5,676,153 | A | 10/1997 | Smith et al. |
| 5,678,562 | A | 10/1997 | Sellers |
| 5,680,102 | A | 10/1997 | Xydis |
| 5,704,351 | A | 1/1998 | Mortara et al. |
| 5,718,233 | A | 2/1998 | Selker et al. |
| 5,724,025 | A | 3/1998 | Tavori |
| 5,725,559 | A | 3/1998 | Alt et al. |
| 5,730,143 | A | 3/1998 | Schwarzberg |
| 5,748,103 | A | 5/1998 | Flach et al. |
| 5,752,976 | A | 5/1998 | Duffin et al. |
| 5,759,199 | A | 6/1998 | Snell et al. |
| 5,772,586 | A | 6/1998 | Heinonen et al. |
| 5,854,994 | A | 12/1998 | Canada et al. |
| 5,868,680 | A | 2/1999 | Steiner et al. |
| 5,931,791 | A | 8/1999 | Saltzstein et al. |
| 5,942,986 | A | 8/1999 | Shabot et al. |
| 5,944,659 | A | 8/1999 | Flach et al. |
| 5,944,669 | A | 8/1999 | Kaib |
| 5,966,692 | A | 10/1999 | Langer et al. |
| 6,016,442 | A | 1/2000 | Hsu et al. |
| 6,064,906 | A | 5/2000 | Langberg et al. |
| 6,091,990 | A | 7/2000 | Hsu et al. |
| 6,093,146 | A | 7/2000 | Filangeri |
| 6,102,856 | A | 8/2000 | Groff et al. |
| 6,184,779 | B1 | 2/2001 | Chen |
| 6,198,394 | B1 | 3/2001 | Jacobsen et al. |
| 6,223,078 | B1 | 4/2001 | Marcovecchio |
| 6,246,907 | B1 | 6/2001 | Lin et al. |
| 6,253,102 | B1 | 6/2001 | Hsu et al. |
| 6,266,554 | B1 | 7/2001 | Hsu et al. |
| 6,272,377 | B1 | 8/2001 | Sweeney et al. |
| 6,287,252 | B1 | 9/2001 | Lugo |
| 6,301,499 | B1 * | 10/2001 | Carlson ............... A61B 5/222 600/510 |
| 6,302,844 | B1 | 10/2001 | Walker et al. |
| 6,366,871 | B1 | 4/2002 | Geva |
| 6,409,661 | B1 | 6/2002 | Murphy |
| 6,411,840 | B1 | 6/2002 | Bardy |
| 6,416,471 | B1 | 7/2002 | Kumar et al. |
| 6,418,340 | B1 | 7/2002 | Conley et al. |
| 6,449,504 | B1 | 9/2002 | Conley et al. |
| 6,470,210 | B1 | 10/2002 | Chen et al. |
| 6,701,183 | B2 | 10/2002 | Baker |
| 6,485,429 | B2 | 11/2002 | Forstner |
| 6,490,479 | B2 | 12/2002 | Bock |
| 6,519,490 | B1 | 2/2003 | Wiesel |
| 6,524,239 | B1 | 2/2003 | Reed et al. |
| 6,564,077 | B2 | 5/2003 | Mortara |
| 6,569,095 | B2 * | 5/2003 | Eggers ............... A61B 5/00 128/903 |
| 6,583,796 | B2 | 6/2003 | Jamar et al. |
| 6,609,023 | B1 | 8/2003 | Fischell et al. |
| 7,263,399 | B2 | 10/2003 | Carlson |
| 6,648,827 | B2 | 11/2003 | Heikkila et al. |
| 6,665,558 | B2 * | 12/2003 | Kalgren et al. ............... 600/510 |
| 6,668,188 | B2 | 12/2003 | Sun et al. |
| 6,687,685 | B1 | 2/2004 | Sadeghi et al. |
| 6,697,655 | B2 | 2/2004 | Sueppel et al. |
| 6,708,057 | B2 | 3/2004 | Morganroth |
| 6,760,620 | B2 | 7/2004 | Sippens Groenewegen |
| 6,793,625 | B2 | 9/2004 | Cavallaro et al. |
| 6,843,801 | B2 | 1/2005 | Conley et al. |
| 6,871,211 | B2 | 3/2005 | Labounty et al. |
| 6,907,284 | B2 | 6/2005 | Hamilton et al. |
| 6,925,324 | B2 | 8/2005 | Shusterman |

(56) References Cited

U.S. PATENT DOCUMENTS

| | | | |
|---|---|---|---|
| 6,934,578 B2 | 8/2005 | Ramseth | |
| 6,937,887 B2 | 8/2005 | Bock | |
| 6,968,227 B2 | 11/2005 | MacAdam et al. | |
| 6,978,169 B1 | 12/2005 | Guerra | |
| 7,001,334 B2 | 2/2006 | Reed et al. | |
| 7,092,751 B2 | 8/2006 | Erkkila | |
| 7,187,965 B2 | 3/2007 | Bischoff et al. | |
| 7,223,234 B2 | 5/2007 | Stupp et al. | |
| 7,311,665 B2 | 12/2007 | Hawthorne et al. | |
| 7,319,900 B2 | 1/2008 | Kim et al. | |
| 7,490,085 B2 | 2/2009 | Walker et al. | |
| 7,532,924 B2 | 5/2009 | Ternes | |
| 7,542,878 B2 | 6/2009 | Nanikashvili | |
| 7,835,910 B1 | 11/2010 | Hakkani-Tur et al. | |
| 8,043,213 B2 | 10/2011 | Hatlestad et al. | |
| 8,187,181 B2 | 5/2012 | Osorio et al. | |
| 2002/0077561 A1* | 6/2002 | Jamar | A61B 5/044 600/510 |
| 2002/0099303 A1 | 7/2002 | Bardy | |
| 2002/0128804 A1 | 9/2002 | Geva | |
| 2002/0143266 A1 | 10/2002 | Bock | |
| 2002/0147409 A1* | 10/2002 | Baker | A61B 5/046 600/518 |
| 2002/0173727 A1 | 11/2002 | Bardy | |
| 2003/0028442 A1 | 2/2003 | Wagstaff et al. | |
| 2003/0069486 A1 | 4/2003 | Sueppel et al. | |
| 2003/0069487 A1 | 4/2003 | Mortara | |
| 2003/0204146 A1 | 10/2003 | Carlson | |
| 2003/0216654 A1* | 11/2003 | Xu | A61B 5/0452 600/509 |
| 2004/0010201 A1 | 1/2004 | Korzinov et al. | |
| 2004/0054294 A1 | 3/2004 | Ramseth | |
| 2004/0059238 A1* | 3/2004 | Fischell | A61B 5/0031 600/515 |
| 2004/0073098 A1 | 4/2004 | Geva et al. | |
| 2004/0093239 A1 | 5/2004 | Ott et al. | |
| 2004/0162497 A1* | 8/2004 | Bennett | A61B 5/0215 600/513 |
| 2005/0119833 A1 | 6/2005 | Nanikashvili | |
| 2005/0203349 A1 | 9/2005 | Nanikashvili | |
| 2007/0100213 A1 | 5/2007 | Dossas et al. | |

FOREIGN PATENT DOCUMENTS

| | | |
|---|---|---|
| EP | 1227752 A1 | 8/2002 |
| EP | 1754440 A1 | 2/2007 |
| JP | 6399840 | 5/1998 |
| JP | 10243930 | 9/1998 |
| JP | 2000195910 A | 7/2000 |
| JP | 2003000559 A | 1/2003 |
| JP | 2003130815 A | 5/2003 |
| JP | 4300523 B2 | 7/2009 |
| WO | WO-93/18710 A1 | 9/1993 |
| WO | WO-2001076461 A2 | 10/2001 |
| WO | WO-2002024276 A1 | 3/2002 |

OTHER PUBLICATIONS

Massimo Santini et al., "Atrial Fibrillation: The Role of Atrial Defibrillation", Journal of Interventional Cardiac Electrophysiology 9, 229-233, 2003.
Med Monitoring Systems, Inc. (Holter, Spiro, OMS, EGG, EKG, APB), http:f/www.medmonitoringsystems.com/ <http://www.medmonitoringsystems.com/> holtertestanalysis2.html [Retrieved Nov. 13, 2003].
Canadian Intellectual Property Office, Application No. 2544926, filed Apr. 28, 2006, in Office Action dated Jun. 22, 2011, 2 pages.
Australian Patent Office, Application No. 2004305423, in office action dated Nov. 23, 2007, 2 pages.
Savi Wireless 0 Mobile Cardiac Telemetry Brochure, published by at least May 2009, 12 pages, Medicomp, Melbourne, Florida.
Crawford, ACC/AHA Guidelines for Ambulatory Electrocardiography, ACC/AHA Practice Guidelines ("ACC Guidelines"), Journal of the American College of Cardiology, vol. 34, No. 3, Sep. 1999, pp. 912-948.
Bock, E., "Atrial Fibrillation Detection for Patient Monitoring," (2002) (Bock II).
*CardioNet, Inc., et al.,* v. *Mednet Healthcare Technologies, Inc., et al.,* Civil Action No. 12-cv-2517, Memorandum, Claim Construction Opinion, Nov. 15, 2013.
*CardioNet, Inc., et al.,* v. *Mednet Healthcare Technologies, Inc., et al.,* Civil Action No. 12-cv-2517 (JS), Plaintiff CardioNet, Inc.'s Opening Claim Construction Memorandum, Jan. 9, 2013.
*CardioNet, Inc.* v. *Mednet Healthcare Technologies, Inc., et al.,* Civil Action No. 12-cv-2517 (JS), Videotaped Deposition of Lev Korzinov, Ph.D., New York, New York, Apr. 11, 2013.
*CardioNet, LLC, et al.,* v. *The ScottCare Corporation, et al.,* Civil Action No. 12-cv-2516 (PBT), Expert Report of Dr. Bryan Bergeron Regarding the Invalidity of U.S. Pat. Nos. 7,212,850; 7,907,996; 6,569,095; 7,587,237; and 7,941,207, Oct. 31, 2014.
*CardioNet, Inc., et al.,* v. *The ScottCare Corporation, et al.,* Civil Action No. 1:12-cv-2516, Memorandum, Claim Construction Opinion, Oct. 8, 2014.
*CardioNet, Inc.,* v. *The ScottCare Corporation, et al.,* Civil Action No. 12-cv-2516 (PBT), Plaintiff CardioNet, Inc.'s Opening Claim Construction Memorandum, Mar. 13, 2013.
*CardioNet, LLC, et al.,* v. *The ScottCare Corporation, et al.,* Civil Action No. 2:12-cv-02516 (PBT), Videotaped Deposition of Lev Korzinov, Ph.D., New York, New York, Aug. 26, 2014.
CardioNet Mobile Outpatient Cardiac Telemetry, Physician Inservice Manual, Document No. 100327, Revision A, Jul. 2002.
*Infobionic, Inc.,* v. *Braemar Manufacturing, LLC,* Before the Patent Trial and Appeal Board, Declaration of Robert T. Stone, Ph.D., U.S. Appl. No. 7,212,850, Aug. 6, 2015.
*Infobionic, Inc.,* v. *Braemar Manufacturing, LLC,* Before the Patent Trial and Appeal Board, Declaration of Robert T. Stone, Ph.D., U.S. Appl. No. 7,907,996, Aug. 6, 2015.
*Infobionic, Inc.,* v. *Braemar Manufacturing, LLC,* Before the Patent Trial and Appeal Board, Petition for Inter Partes Review of U.S. Appl. No. 7,212,850, Aug. 10, 2015.
*Infobionic, Inc.,* v. *Braemar Manufacturing, LLC,* Before the Patent Trial and Appeal Board, Petition for Inter Partes Review of U.S. Appl. No. 7,907,996, Aug. 10, 2015.
Park, S. et al., "Cardiac Surveillance at Home," EP Lab Digest, Nov. 2002.
Tateno et al., "Automatic detection of atrial fibrillation using the coefficient of variation and density histograms of RR and ΔRR intervals," Medical & Biological Engineering & Computing 2001, vol. 39, pp. 664-671.
Cuesta, Biosignal Laboratory: A Software: Tool for Biomedical Signal Processing and. Analysis, Proceedings of the 25th Annual International Conference of the IEEE EMBS, pp. 3544-3547, Sep. 17, 2003.
Jane, Evaluation of an Automatic Threshold Based Detector of Waveform Limits in Holter ECG with the QT Database, Computers in Cardiology 1997, pp. 295-298, Jul. 10, 1997.
Zong, Automated ECG Rhythm Analysis Using Fuzzy Reasoning, Computers in Cardiology 1998, pp. 69-72, Sep. 13, 1988.
Petition for Inter Partes Review of U.S. Pat. No. 7,212,850.
Petition for Inter Partes Review of U.S. Pat. No. 7,907,996.
*CardioNet, LLC and Braemark Manufacturing, LLC* v. *Infobionic, Inc.,* Civil Action No. 1:15-cv-11803-IT, Joint Claim Construction and Prehearing Statement, Oct. 31, 2016.
Coumel, Clinical Approach to Paroxysmal Atrial Fibrillation, Clin. Cardiol. vol. 13, at 209-212.
Cuesta, Biosignal Laboratory: A Software: Tool for Biomedical Signal Processing and Analysis, Proceedings of the 25th Annual International Conference of the IEEE EMBS, pp. 3544-3547.
Falk Ch. 15, Pharmacologic Control of Ventricular Rate in Atrial Fibrillation, in Atrial Fibrillation: Mechanisms and Management, 2d Ed., at 299, 307-311.
Falk Ch. 24, Clinical Management of Atrial Fibrillation: An Overview, in Atrial Fibrillation: Mechanisms and Management, 2d Ed., at 491, 493.

(56) References Cited

OTHER PUBLICATIONS

Hnatkova, Analysis of the Cardiac Rhythm Preceding Episodes of Paroxysmal Atrial Fibrillation, Am. Heart J., vol. 135, No. 6, Pt. 1, at 1012.

Kosara, Visualization Methods for Data Analysis and Planning in Medical Applications, Int'l J. of Med. Informatics, 68 (2002), 141-153, at Abstract, 141, 145, 145-146.

Otsuka, Ambulatory ECG-Respiration Monitoring System, Abstract, Proceedings of the 10th Int'l Congress of Biometeorology, at 130.

Powsner, Graphical Summary of Patient Status, Lancet, vol. 344, at 386.

Tufte, The Visual Display of Quantitative Information, 2d Ed., at 30. Mar. 10, 2008, CA2544926; Office Action From CA Intellectual Property Office.

Biomedical Computer Laboratory, Institute for Biomedical Computing, Washington University, "Progress Report No. 21," Jul. 1, 1984-Jun. 30, 1985, 164 pages.

Canadian Intellectual Property Office, Application No. 2,544,926, dated Mar. 10, 2008, 3 pages.

European Patent Office, Application No. 04702945.9, filed Jan. 16, 2004, in Supplementary Partial European Search Report, dated Nov. 11, 2010, 4 pages.

Japanese Patent Application No. 2006-541106, Dispatch Date Nov. 4, 2009, Notification of Reason(s) for Refusal, with translation, 7 pages.

Getzow, Scot M., Authorized Officer, International Searching Authority, Application No. PCT/US04/01107, filed Jan. 16, 2005.

Jan Galuszka et al., "Assessment of Spectral Analysis of Heart Rate Variability in Patients With History of Atrial Fibrillation by Means of Age-Dependent Parameters", Biomed. Papers 146(2), 81-85 (2002).

Japanese Patent Office, dated Nov. 4, 2009, Office Action for Application No. JP2006-5411006.

Jun. 20, 2009, JPO Office Action for patent application No. 2006-541106.

\* cited by examiner

SYSTEM AND METHOD FOR PROCESSING AND PRESENTING ARRHYTHMIA INFORMATION TO FACILITATE HEART ARRHYTHMIA IDENTIFICATION AND TREATMENT

CROSS REFERENCE TO RELATED APPLICATIONS

This application is a continuation of the U.S. patent application Ser. No. 13/046,673, filed Mar. 11, 2011, which is a continuation of U.S. patent application Ser. No. 11/739,037, filed Apr. 23, 2007, which is a continuation application of and claims the benefit of priority from the U.S. Application entitled "System And Method For Processing And Presenting Arrhythmia Information To Facilitate Heart Arrhythmia Identification And Treatment," filed Jan. 16, 2004, application Ser. No. 10/760,122, and claims priority from U.S. Provisional Application entitled "Presenting Arrhythmia Information to Facilitate Heart Arrhythmia Identification and Treatment," filed Nov. 26, 2003, Application Ser. No. 60/525,386, the contents of which are incorporated herein by reference in their entirety.

BACKGROUND

The present application describes systems and techniques relating to processing and presenting arrhythmia event information from physiological data, for example, selectively presenting atrial fibrillation events to a medical practitioner.

Over the years, various devices have been used for monitoring hearts in living beings. Additionally, systems have been used to collect and report on heart information obtained from patients.

SUMMARY

In general, in one aspect, a heart monitoring system collects heart data from a monitored individual and stores the data at a monitoring center. Collected data can be processed, and graphical representations of the collected information can be presented to medical practitioners to assist in treating heart arrhythmias, such as atrial fibrillation. A system and method can involve operations including identifying arrhythmia events in physiological data obtained for a living being, receiving human assessments of at least a portion of the arrhythmia events, determining a measure of correlation between the human assessments and the identified events, and selectively presenting information regarding the identified events based on the measure of correlation. The operations also can include identifying atrial fibrillation events in physiological data obtained for a living being, obtaining heart rate data for the living being, and presenting information regarding the heart rate data and duration of the atrial fibrillation events together with a common time scale to pictographically represent heart rate trend with atrial fibrillation burden during a defined time period.

One or more of the following advantages can be realized. The heart monitor can loop every twenty-four hours and can automatically transmit heart data at least every twenty-four hours. The system can automatically generate a daily graphical summary of atrial fibrillation (AF) burden for review by a medical practitioner, which can be presented effectively anywhere using one or more communication networks. The AF burden graph can be used for asymptomatic AF detection, drug therapy (rate, rhythm, anti-coagulants), pre/post ablation monitoring, and CHF (congestive heart failure) decompensation. The system can provide an overall sensitivity of 96%, a positive predictivity of over 99%, and artifact rejection of over 90%. In one implementation, the graph only displays events where AF detection is validated by a technician finding AF in over 50% of the automatically identified events.

The details of one or more embodiments are set forth in the accompanying drawings and the description below. Other features and advantages will become apparent from the description, the drawings, and the claims.

DRAWING DESCRIPTIONS

DETAILED DESCRIPTION

Figure 1:
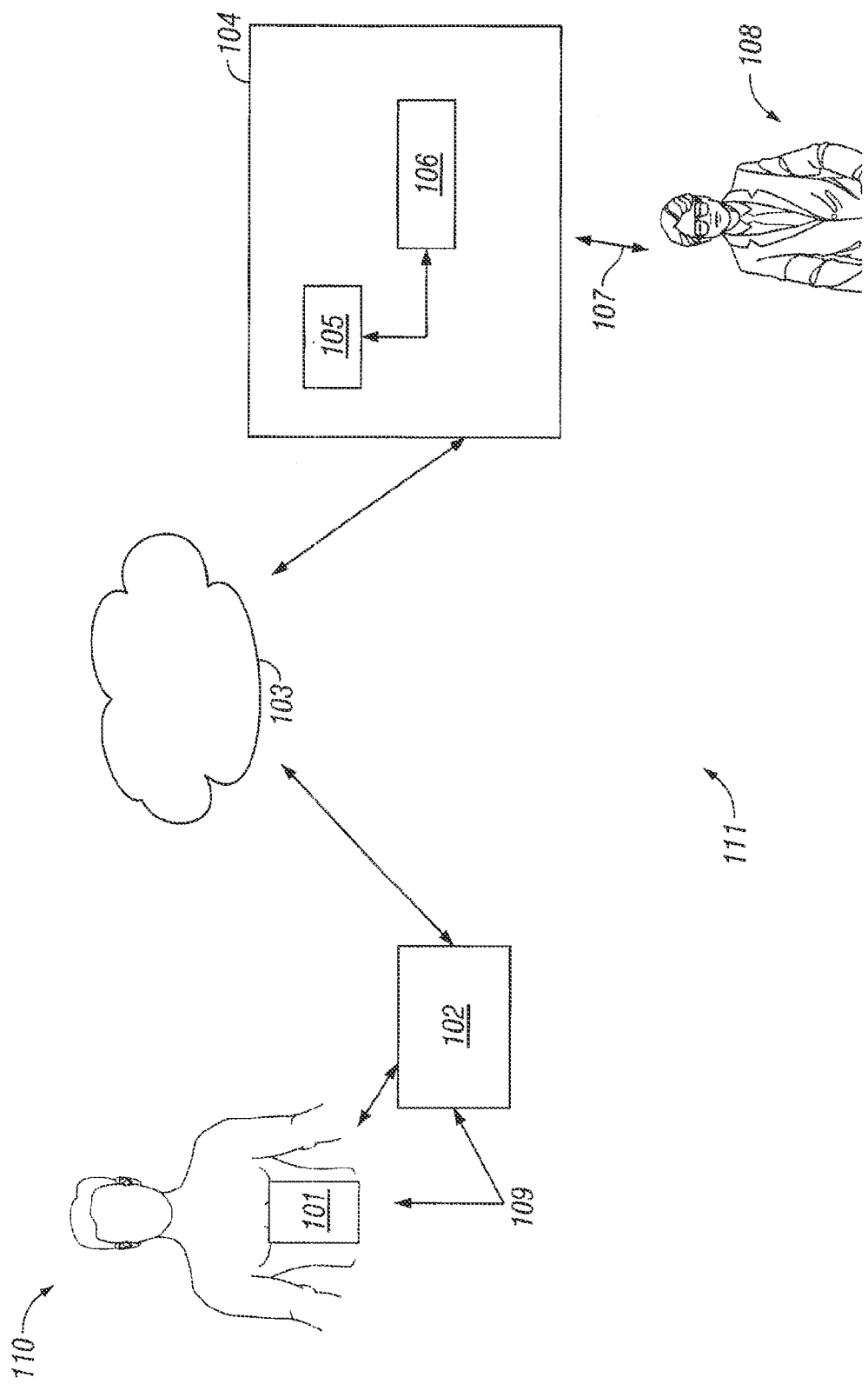
FIG. 1 illustrates, according to an exemplary embodiment, a system for reporting information related to arrhythmia events.

FIG. 1 illustrates, according to one embodiment, a system for reporting information related to arrhythmia events, such as atrial fibrillation events. In this embodiment, monitoring system 109 can communicate (via devices 101 and 102) ECG (electrocardiogram), cardiac event, and other data to monitoring center 104. The system 109 can include, for example, an implantable medical device (IMD), such as an implantable cardiac defibrillator and an associated transceiver or pacemaker and an associated transceiver, or a monitoring device 101 that a patient 110 wears. Further, monitoring system 109 can include a monitor processing device 102 that can send standard physiological data (received from monitoring device 101) to monitoring center 104 and that can detect arrhythmia events (such as atrial fibrillation events). In one implementation, the devices 101 and 102 are integrated into a single device. Moreover, the system 109 can be implemented using, for example, the CardioNet Mobile Cardiac Outpatient Telemetry (MCOT) device, which is commercially available and provided by CardioNet, Inc of San Diego, Calif.

Monitor processing device 102 can transmit physiological data (including data related to arrhythmia events) through a communication network 103, which can be a local area network (LAN), a landline telephone network, a wireless network, a satellite communication network, or other suitable network to facilitate two-way communication with monitoring center 104. Advantageously, monitoring center 104 can be located in the same location (e.g., in the same room or building) as monitoring system 109 or at some remote location.

The monitoring center 104 can include a monitoring (or display) station 105 and a processing system 106. In one implementation, a cardiovascular technician (CVT) can use the monitoring station 105 to evaluate physiological data received from monitoring system 109, identifying and reporting, among other things, arrhythmia events (such as atrial fibrillation events). The CVT reports these assessments of the physiological data to the processing system 106, which also receives information related to the arrhythmia events identified by monitoring system 109. As will be explained further below, processing system 106 analyzes this arrhythmia event data (both the human-assessed data from the CVT and the data reported by monitoring system 109) and determines whether to generate a graph (or other similar presentation) related to these events. In certain circumstances, the processing system will send a report related to both arrhythmia and heart rate data to, for example, a physician or other health care provider 108 via transmission path 107—which may be part of the network 103.

Figure 3:
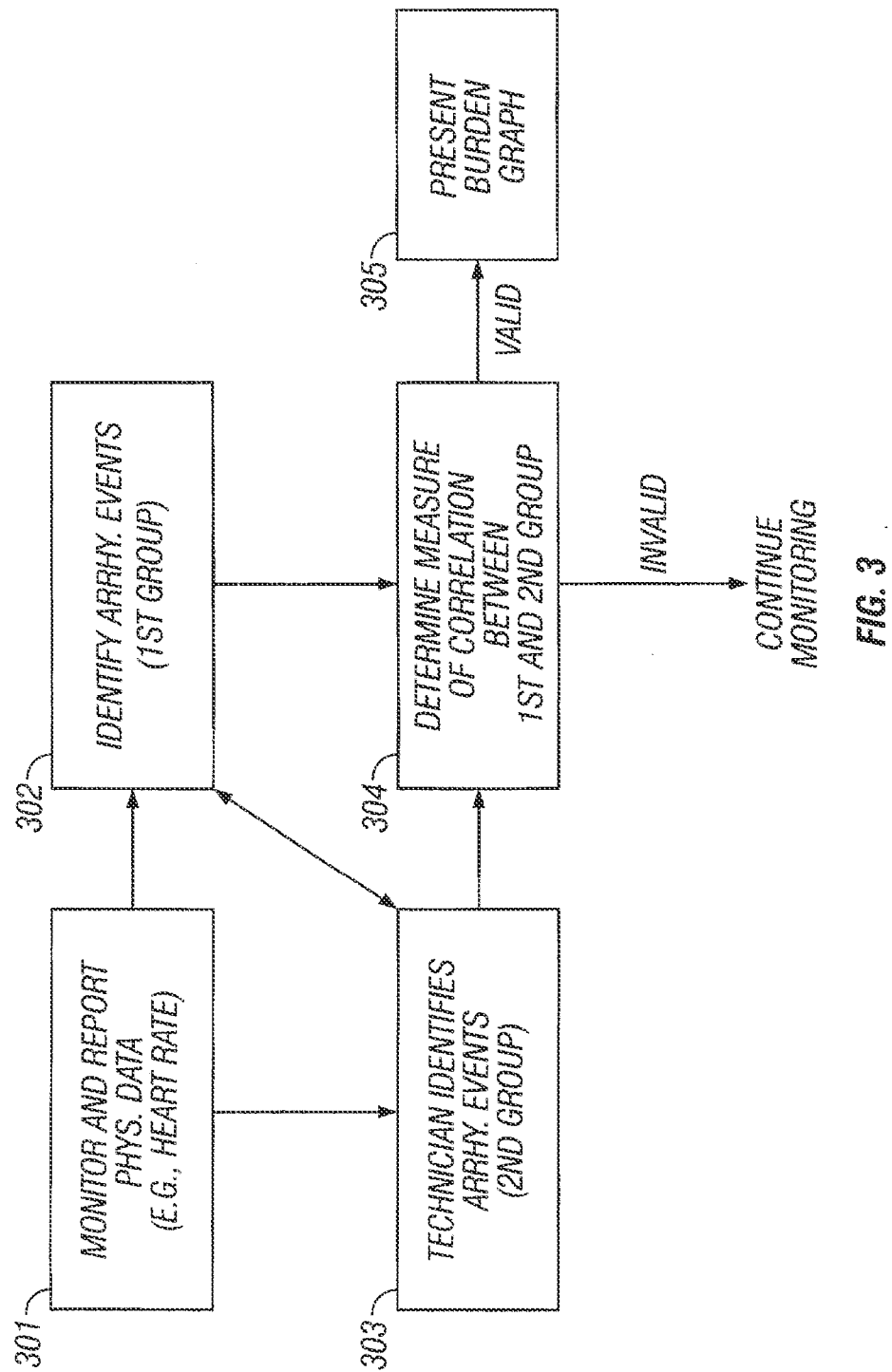
FIG. 3 is a diagram illustrating, according to an exemplary embodiment, a procedure for monitoring, processing, and reporting information related to arrhythmia events.

FIG. 3 illustrates, according to one embodiment, a procedure for monitoring, processing, and reporting arrhythmia event data (such as data associated with atrial fibrillation events). In this embodiment, the monitoring system 109 (illustrated in FIG. 1) monitors and reports physiological data (including data related to heart rate) at 301. At 302, various parts of this physiological data can be analyzed (for example, RR variability and QRS morphology) and arrhythmia events can be identified based on predefined criteria—the information relating to these events (among other possible information) constituting a first group of data. In one implementation, the monitoring system 109 identifies certain of the arrhythmia events that are urgent or representative and reports those events to both a CVT at 303 and to the processing system at 304. Alternatively, the system could simply report the events identified at 302 to the processing system. Further, at 303, a CVT, using station 105, evaluates various parts of the physiological data received from 302 and/or 301 and also identifies arrhythmia events—the information relating to these human-assessed events (among other possible information) constituting a second group of data. Here, if needed, the CVT can request additional data from monitoring system 109.

At 304, the processing system 106 analyzes both the first and second group of data, determining a measure of correlation between these groups. This process can involve, for example, determining whether a correlation measure exceeds and/or equals a predetermined correlation parameter or whether a correlation measure is less than and/or equals that parameter. If, based on the correlation analysis, the information related to the arrhythmia events is determined to be valid, then the system generates a report relating to both heart rate trend and the arrhythmia events at 305, such as the graph shown in FIG. 2 or the graphs shown in FIG. 4. If, on the other hand, there is insufficient correlation, then the system does not generate a report and monitoring continues.

To illustrate, in one implementation, every ten minutes, the monitoring system 109 transmits a "flag" if it has detected an atrial fibrillation (AF) event in the last ten minutes. In this implementation, the processing system 106 only generates a graph (or graphs) related to heart rate trend and atrial fibrillation burden such as the graph shown in FIG. 2 or the graphs shown in FIG. 4—if more than 50% of the ten minute flags (generated at 302) match events identified by a CVT (at 303)—a correlation (with respect to the time period at issue) indicating a high positive predictivity for the identification of AF events. If this 50% threshold is not met, then the system does not generate a graph (or graphs) based on the data at issue and simply continues to process data.

The term "atrial fibrillation burden" (or more generally, "arrhythmia event burden") refers generally to the overall amount of time that a patient is in atrial fibrillation (or arrhythmia) over a specified time period, taking into account the number and duration of episodes. Advantageously, employing pictographic presentations, such as those of FIGS. 2 and 4, a medical practitioner can see whether a patient is more likely to experience an arrhythmia, such as AF, at certain times of the day, and this can affect therapeutic approaches in some cases.

Figure 2:
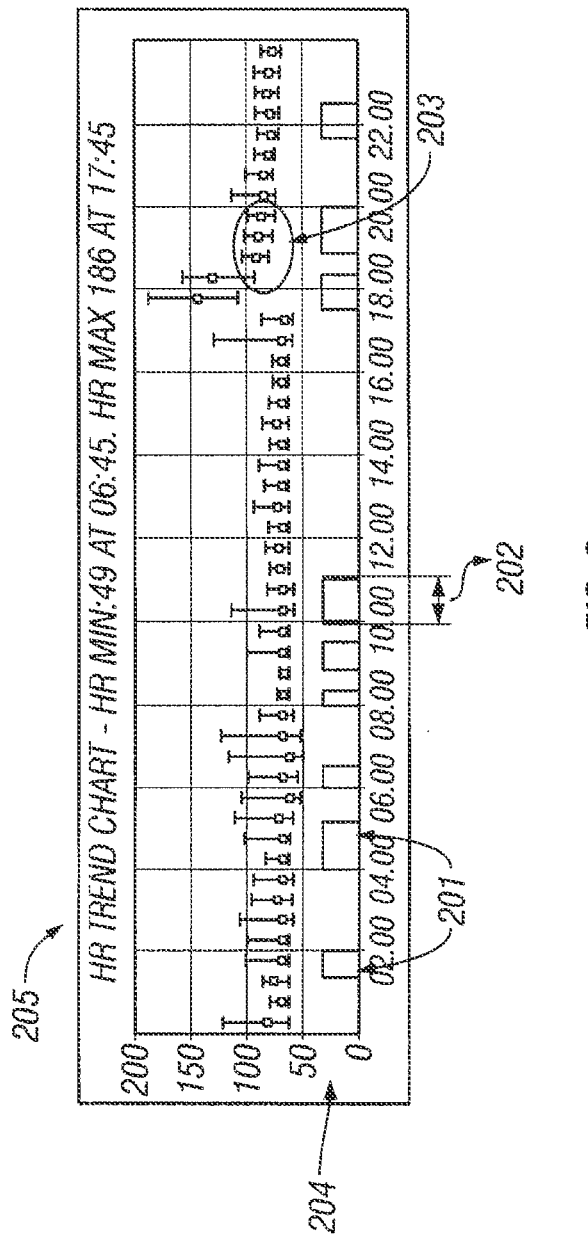
FIG. 2 shows, according to one embodiment, a graph presenting an example of atrial fibrillation burden and heart rate trend.

FIG. 2 represents one example of how to pictographically present both heart rate trend and atrial fibrillation burden on a common time scale (to "pictographically present" such data, however, a graph is not required.). The graph 205 contains information relating to, for example, daily AF incidence and time of occurrence 201, AF duration 202, and heart rate (203 and 204). A scale 204 (in this example) indicates heart rate in average beats-per-minute and the dots and lines shown at 203 (for example) indicate values on that scale, standard deviations associated with these values, and heart rates during AF. Further, graph 205 shows heart rate data at 15 minutes and 45 minutes past the hour. Finally, in this graph, the presence of one or more AF events in a given 10-minute period is graphed as a 10-minute interval.

Figure 4:
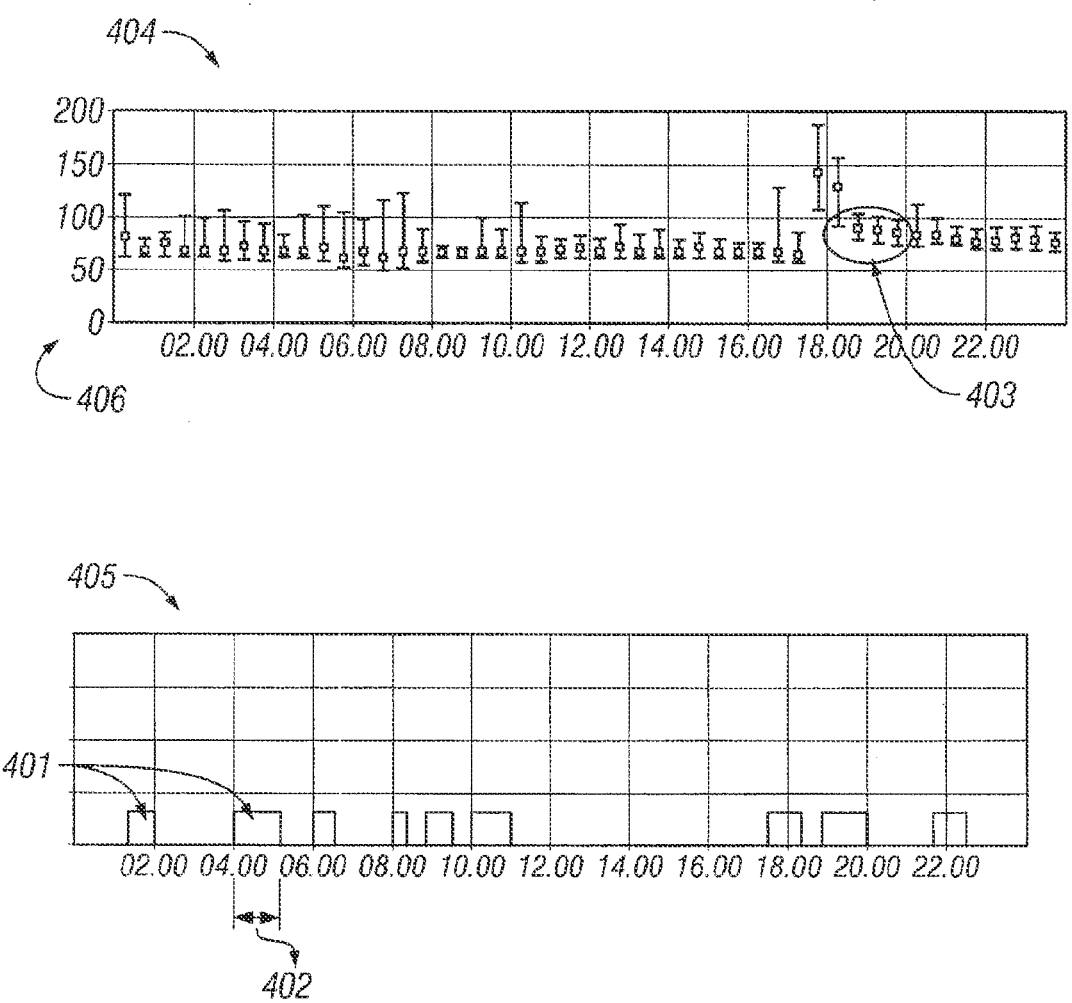
FIG. 4 shows, according to an exemplary embodiment, one graph presenting an example of atrial fibrillation burden and one graph presenting an example of heart rate trend.

Like FIG. 2, FIG. 4 represents an example of how to pictographically present heart rate trend and atrial fibrillation burden on a common time scale. Although FIG. 4, unlike FIG. 2, uses two graphs, FIG. 4 presents the same information as FIG. 2. Specifically, graphs 404 and 405 contain information relating to, for example, daily AF incidence and time of occurrence 401, AF duration 402, and heart rate (403 and 406). A scale 406 (in this example) indicates heart rate in average beats-per-minute and the dots and lines shown at 403 (for example) indicate values on that scale, standard deviations associated with these values, and heart rates during AF.

Figure 5:
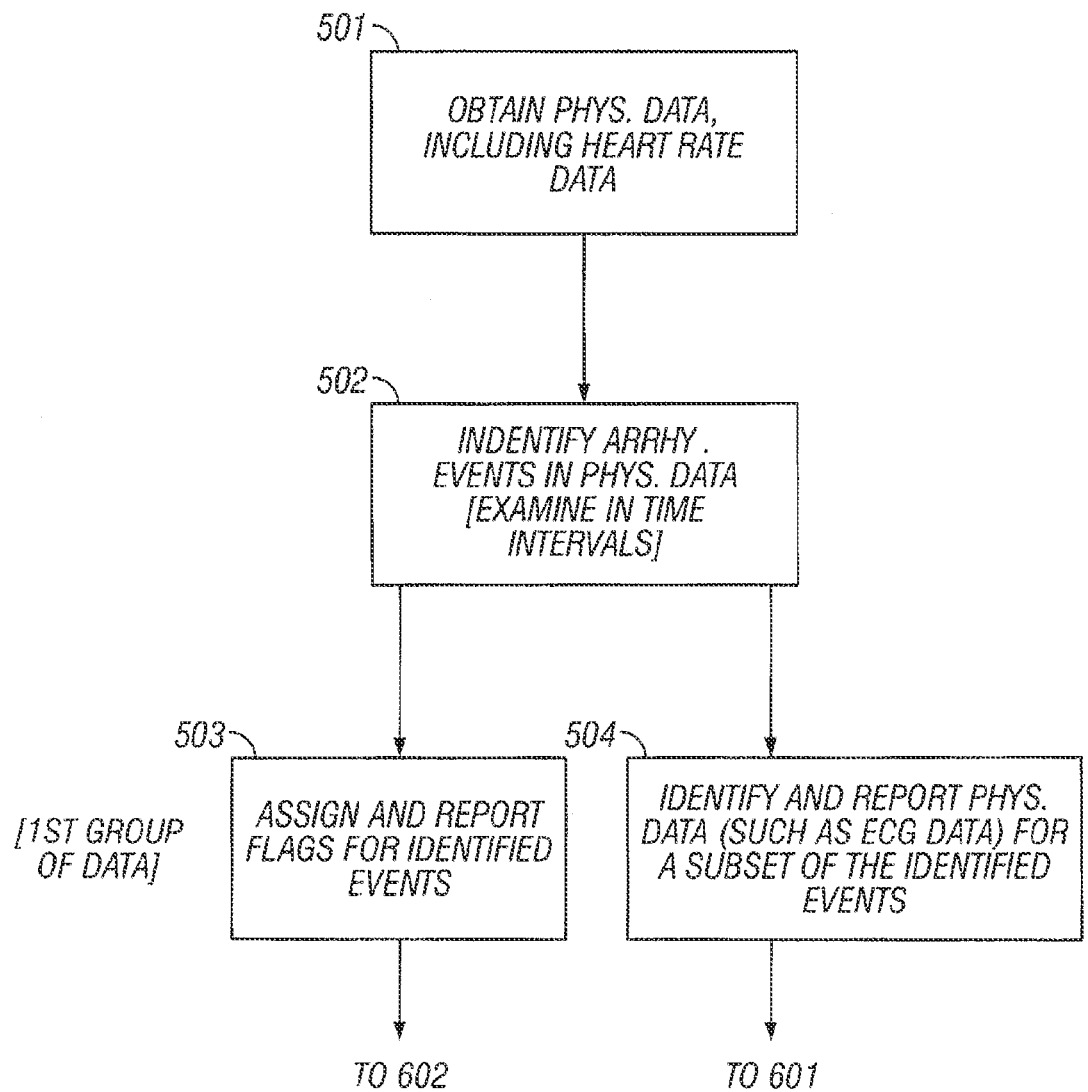
FIGS. 5 and 6 are diagrams illustrating, according to another exemplary embodiment, a procedure for monitoring, processing, and reporting information related to arrhythmia events.
Figure 6:
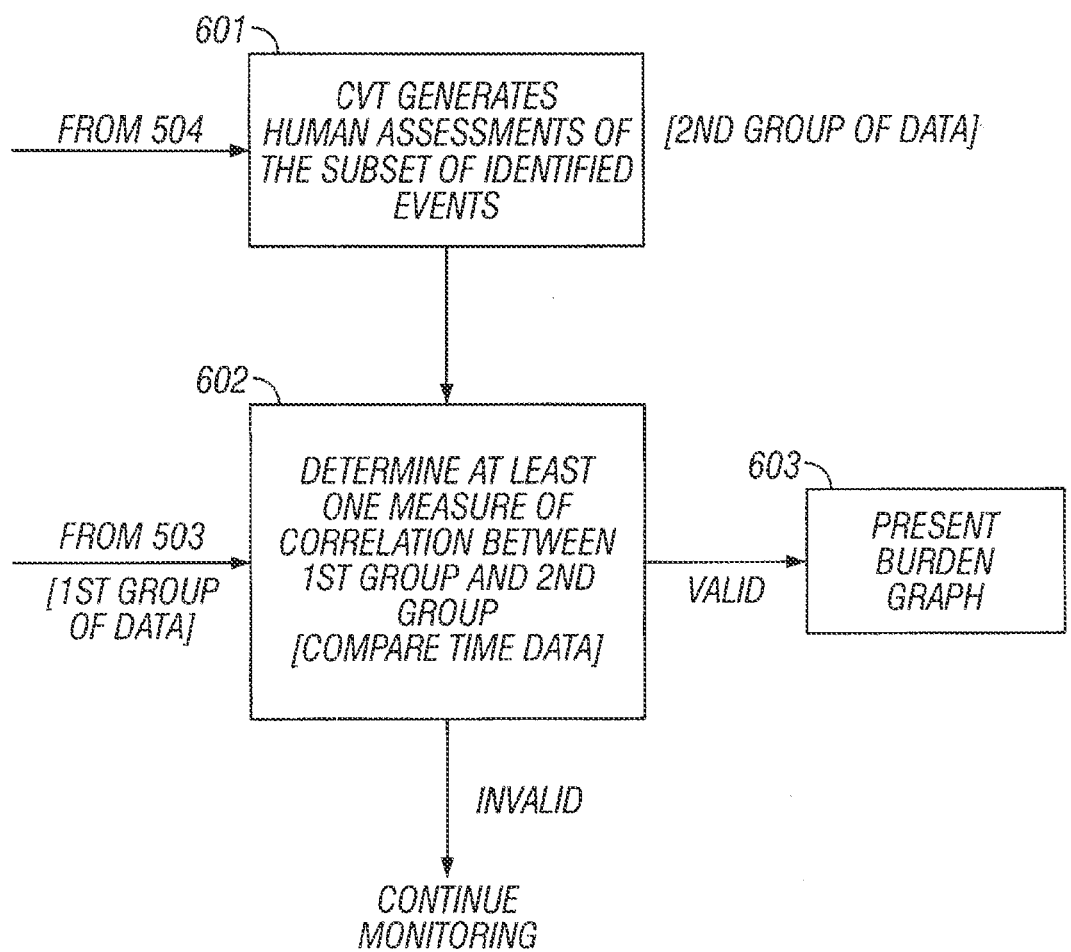

FIGS. 5 and 6 are diagrams illustrating another implementation of the invention. Specifically, at 501, the system 111, employing monitoring system 109, obtains physiological data, including heart rate data. In turn, at 502, the system identifies the presence of arrhythmia events (such as AF events) in this physiological data, examining this data in time intervals. At 503, the system assigns flags indicating the presence of arrhythmia events and reports those flags—which represent a first group of data—to the processing system. Similarly, at 504, the system identifies and reports physiological data, such as ECG data, for a subset of the events identified at 502 and reported at 503. Notably, the system, in this implementation, need not report physiological data for each flag assigned at 503, but need only report data associated with the most significant events identified at 502, thereby minimizing the data sent to a CVT.

At 601, the CVT analyzes this data and reports whether arrhythmia events have occurred, thereby generating a second group of data. The processing system then determines (at 602), based on comparing time stamps associated with each group of data, at least one measure of correlation between the first group of data and the second group of data. To illustrate, if enough of the human-assessed events reported at 601 match the events reported at 503, then the system determines that the data is valid, that is, that there is a high positive predictivity for the identification of arrhythmia events. If such a determination is made, the data associated with each flag reported at 503 is pictographically presented in a form such as FIG. 2 or FIG. 4. Significantly, in this implementation, while this pictographic representation can contain all such data, the CVT need only review a subset of this data. In short, the system achieves increased accuracy in the presentation of information relating to arrhythmia events while minimizing the data that the CVT reviews.

The disclosed system and all of the functional operations described and illustrated in this specification can be implemented in digital electronic circuitry, or in computer hardware, firmware, software, or in combinations of the forgoing. Apparatus can be implemented in a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

To provide for interaction with a user (such as the CVT), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

Finally, while the foregoing system has been described in terms of particular implementations, other embodiments are within the scope of the following claims. For example, the disclosed operations can be performed in a different order and still achieve desirable results. Moreover, the system need not employ 10-minute intervals; many different time intervals are possible (as is no interval at all), including 1 minute, 30 second, and 30-minute intervals. Indeed, because time intervals are not required, the graphs of FIGS. 2 and 4 could be modified to show continuous heart rate trend (accompanied by corresponding AF data) rather than just specific instances of this trend. Further, while FIGS. 2 and 4 show examples of (among other things) pictographically presenting atrial fibrillation burden (one type of arrhythmia event burden), one could present the same or similar information for another type of arrhythmia event. In fact, one could employ both the format and procedures associated with generating FIG. 2 or FIG. 4 (or a similar figure) to pictographically present information related to a number of different types of arrhythmia event burdens.

What is claimed is:

1. A method comprising:
obtaining a physiological signal for a living being;
performing, using a computer implemented process, a first assessment of the physiological signal over a first time period consisting of a plurality of time intervals, wherein each of the plurality of time intervals has a uniform time length;
based on performing the first assessment of the physiological signal, identifying multiple arrhythmia events of a first type and multiple arrhythmia events of a second type in the physiological signal, wherein identifying the multiple arrhythmia events of the first type and the multiple arrhythmia events of the second type comprises:
examining the physiological signal in each of the plurality of time intervals;
identifying first time intervals based on at least one arrhythmia event of the first type occurring during each of the first time intervals; and
identifying second time intervals based on at least one arrhythmia event of the second type occurring during each of the second time intervals;
obtaining heart rate data for the living being; and
pictographically presenting, using a common time scale:
the heart rate data;
indications of the identified multiple arrhythmia events of the first type; and
indications of the identified multiple arrhythmia events of the second type, wherein:
pictographically presenting the indications of the identified multiple arrhythmia events of the first type comprises pictographically presenting, on the common time scale, first markers having the uniform time length and representing the identified first time intervals; and
pictographically presenting the indications of the identified multiple arrhythmia events of the second type comprises pictographically presenting, on the common time scale, second markers having the uniform time length and representing the identified second time interval;
wherein the uniform time length is 30 seconds, 1 minute, 10 minutes, or 30 minutes.

2. The method of claim 1, further comprising pictographically presenting an indication of a maximum heart rate during a time period and a time during the time period when the maximum heart rate occurred.

3. The method of claim 1, further comprising pictographically presenting an indication of a minimum heart rate during a time period and a time during the time period when the minimum heart rate occurred.

4. The method of claim 1, further comprising:
identifying a first subset of the identified multiple arrhythmia events of the first type as urgent;
wherein pictographically presenting the indications of the identified multiple arrhythmia events of the first type comprises pictographically presenting indications of the first subset of the identified multiple arrhythmia events of the first type.

5. The method of claim 1, further comprising:
identifying a first subset of the identified multiple arrhythmia events of the first type as representative;
wherein pictographically presenting the indications of the identified multiple arrhythmia events of the first type comprises pictographically presenting the indications of the first subset of the identified multiple arrhythmia events of the first type.

6. The method of claim 1, further comprising:
receiving a second assessment of a portion of the physiological signal associated with a corresponding portion of the physiological signal;
determining that the identified multiple arrhythmia events of the first type are valid when a threshold of the identified multiple arrhythmia events of the first type match arrhythmia events of the first type identified by the second assessment; and
determining that the identified multiple arrhythmia events of the second type are valid when a threshold of the identified multiple arrhythmia events of the second type match arrhythmia events of the second type identified by the second assessment.

7. The method of claim 6, wherein obtaining the physiological signal for the living being comprises obtaining ECG data from a mobile monitoring system, and wherein the second assessment comprises requesting additional ECG data from the mobile monitoring system.

* * * * *